United States Patent
Dong et al.

[11] Patent Number: 5,902,605
[45] Date of Patent: May 11, 1999

[54] DRUG DELIVERY DEVICE WITH MINIMAL RESIDUAL DRUG RETENTION

[75] Inventors: Liang C. Dong, Sunnyvale; Patrick S.-L. Wong, Palo Alto; Si-Hong Yum, Dale City; Crystal Pollock, Mountain View, all of Calif.

[73] Assignee: Alza Corporation, Palo Alto, Calif.

[21] Appl. No.: 08/851,525

[22] Filed: Apr. 18, 1997

Related U.S. Application Data

[60] Provisional application No. 60/015,567, Apr. 18, 1996.

[51] Int. Cl.$^6$ ..................................................... A61K 9/22
[52] U.S. Cl. ........................ 424/453; 424/451; 424/463; 424/473; 424/438; 424/462
[58] Field of Search ................................ 424/451, 463, 424/473, 438, 453, 462; 604/892.1, 890.1

[56] References Cited

U.S. PATENT DOCUMENTS

| | | | |
|---|---|---|---|
| 3,845,770 | 11/1974 | Theeuwes et al. | 128/260 |
| 3,865,108 | 2/1975 | Hartop | 128/260 |
| 3,995,631 | 12/1976 | Higuchi | 128/260 |
| 4,002,173 | 1/1977 | Manning et al. | 128/296 |
| 4,034,756 | 7/1977 | Higuchi et al. | 128/260 |
| 4,111,202 | 9/1978 | Theeuwes | 128/260 |
| 4,207,893 | 6/1980 | Michaels | 128/260 |
| 4,265,874 | 5/1981 | Bonsen et al. | 424/15 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,595,583 | 6/1986 | Eckenhoff et al. | 424/15 |
| 4,612,008 | 9/1986 | Wong et al. | 604/892 |
| 4,874,388 | 10/1989 | Wong et al. | 604/891.1 |
| 5,198,229 | 3/1993 | Wong et al. | 424/473 |
| 5,312,388 | 5/1994 | Wong et al. | 604/892.1 |
| 5,312,390 | 5/1994 | Wong | 604/892.1 |
| 5,358,502 | 10/1994 | Herbig et al. | 604/892.1 |
| 5,443,459 | 8/1995 | Wong et al. | . |
| 5,498,255 | 3/1996 | Wong | . |
| 5,630,808 | 5/1997 | Magruder et al. | . |
| 5,714,160 | 2/1998 | Magruder et al. | . |
| 5,728,088 | 3/1998 | Magruder et al. | . |
| 5,750,143 | 5/1998 | Rashid et al. | . |

FOREIGN PATENT DOCUMENTS 0384642  8/1990  European Pat. Off. ......... A61K 9/22

*Primary Examiner*—Thurman K. Page
*Assistant Examiner*—Brian K. Seidleck
*Attorney, Agent, or Firm*—John A. Dhuey; Steven F. Stone; Michael J. Rafa

[57] ABSTRACT

The present invention is directed to a fluid-imbibing drug delivery device which is useful for the initial delayed delivery of an active agent formulation to a fluid environment of use, the initial delay period to startup or activation of the device being of a predetermined length of time. The delivery of the agent formulation from the dispensing device is continued until essentially all of the active agent formulation is delivered as a result of the fluid inhibition into a fluid flow path in the housing of the device and the expansion of an expansion agent in the active agent delivery chamber.

17 Claims, 2 Drawing Sheets

DRUG DELIVERY DEVICE WITH MINIMAL RESIDUAL DRUG RETENTION

This application claims priority of U.S. Provisional application No. 60/015,567, filed Apr. 18, 1996.

FIELD OF THE INVENTION

The present invention is related to the delayed delivery of an active agent to a fluid environment of use, where the active agent is minimally retained in the delivery device. More particularly, the invention is an active agent delivery device that allows for water infiltration into the device to ensure release of the active agent from the device.

BACKGROUND OF THE INVENTION

Oral delivery of therapeutically active agents is a convenient and cost effective method of delivery. The active agent can be released in the mouth or anywhere in the alimentary canal. The delivery can be in a bolus, it can be intermittent, or it can be continuous.

Osmotic dispensing devices for delivery of therapeutically active agents are well known in the art. Such devices use an expansion means to deliver an agent to an environment of use over a period of hours, days or months. The expansion means absorbs liquid, expands, and acts to drive out the beneficial agent formulation from the interior of the device in a controlled, usually constant manner. The osmotic expansion means is used to controllably, usually relatively slowly, and over a period of time, deliver the agent.

Osmotic devices have also been described for prolonged and controlled delivery of one or more active agents where an initial delay of delivery is desired. U.S. Pat. No. 5,198,229, which is incorporated herein by reference, is directed to an osmotic device for delivery of an active agent to the upper gastrointestinal tract. The dispensing device comprises concentric housings that are in slidably telescoping arrangement with each other. A first expansion means imbibes fluid when placed in the stomach environment. This expansion means expands and pushes against a partition layer that in turn pushes against an active agent formulation. The active agent is delivered to the stomach environment through a small exit port in a controlled and continuous manner. After all the active agent has been delivered, the housings separate, the buoyancy chamber is exposed to the stomach environment, the density of the device increases, and the device sinks and exits out of the stomach.

U.S. Pat. No. 5,312,388, which is incorporated herein by reference, describes the use of slidably telescopic concentric housings in an osmotic device where delivery of more than one active agent is desired or where separate dosings of one active agent is desired. In a particular embodiment, initial rapid delivery of a particular active agent is followed by delayed delivery of the active agent. A loading dose of the active agent is dispensed as soon as the device enters the environment of use. Prolonged delivery is accomplished as a result of an expansion means that imbibes fluid and expands to separate the concentric housings. Upon separation, the active agent contained within the housings is dispensed.

U.S. Pat. No. 5,312,390, which is incorporated herein by reference, describes an osmotic device useful for the initially delayed delivery of an active agent. Slidably telescoping concentric housings separate following absorption of fluid through the housing. A fluid passage means is exposed to the fluid environment and the active agent is expelled in a controlled and continuous manner through an exit port at the end of the housing opposite the fluid passage means.

U.S. Pat. No. 5,358,502, which is incorporated herein by reference, describes an osmotic device with a semipermeable membrane with an agent that is pH sensitive and thus will dissolve at a given pH, thereby releasing the contents of the device.

Bolus delivery of an active agent is described in U.S. patent application Ser. No. 08/459,387, which is incorporated herein by reference. The patent application describes a fluid-imbibing drug delivery device that is useful for the delayed delivery of drug. A first and second housing are in reversibly sliding telescoping arrangement. The first housing contains an active agent and a first expansion agent. The second housing contains a second expansion agent. The second expansion agent imbibes fluid and pushes apart the housings. The drug is delivered and the first expansion agent imbibes fluid and expands to push any remaining drug out of the device.

As can be observed in the above-referenced patents and patent applications, osmotic devices have been described that provide for an initial pulse of an active agent, that provide for prolonged delivery of an active agent, and that provide for delivery of more than one active agent. However, there remains a continuing need for improved methods and systems for delivering one or more active agents in a reliable and reproducible manner.

SUMMARY OF THE INVENTION

We have observed that devices such as those described above will open in a predictable manner but that the agent contained in the device may not always be completely released to the environment of use following the desired delay period. Accordingly, the present invention is directed to a fluid-imbibing dispensing device and a method for the essentially complete delivery of an active agent to a fluid environment of use following an initially delayed period of delivery of the agent.

In one aspect, the invention is directed to a fluid-imbibing delivery device formed of a housing and a closure for the housing. The housing contains an active agent formulation and a first expansion agent. The active agent formulation comprises at least one active agent. The housing is configured to provide a flow path between the interior of the housing and the active agent formulation. The closure comprises a second expansion agent.

The invention is further directed to a device for dispensing an active agent formulation to an environment of use following an initial period of delay, that comprises a housing with a closed end and an open end. The housing contains an active agent formulation that comprises at least one active agent. The housing further contains an expansion agent. The device further comprises a plug sealing the open end of the housing. The improvement of the invention comprises a fluid flow path between the interior of the housing and the active agent formulation.

The invention is also directed to a device for dispensing an active agent formulation to an environment of use following an initial period of delay, that comprises a first impermeable housing and a second semipermeable housing. The first and second housings are in reversibly sliding telescoping arrangement with each other. The first housing contains an active agent formulation that comprises at least one active agent. The first housing further contains a first expansion agent. The second housing contains a second expansion agent. The improvement of the invention comprises a fluid flow path between the interior of the first housing and the active agent formulation.

BRIEF DESCRIPTION OF THE DRAWINGS

The drawings are not drawn to scale, but are set forth to illustrate various embodiments of the invention. Like numbers refer to like structures.

DETAILED DESCRIPTION OF THE INVENTION

Figure 1:
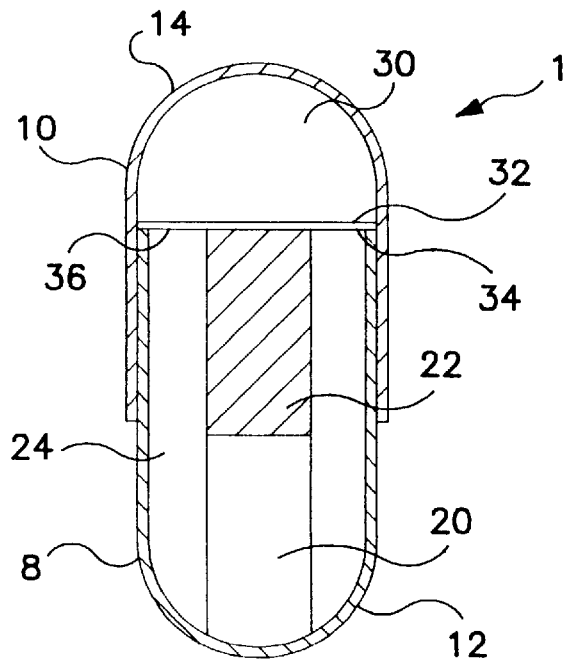
FIG. 1 is a side cross-sectional view of one embodiment of a delivery device according to the present invention, the device being in closed or prepared form prior to placement in the environment of use.

The present invention provides a device which is useful for delivering an active agent formulation to a fluid environment of use. There is an initial delay period to startup or activation of the device, this delay period lasts a predetermined length of time, and is followed by essentially complete delivery of the active agent formulation to the environment of use.

DEFINITIONS

The phrase "initial delay period" intends a period of about a few minutes to a period of about a day, preferably between about 1 and 24 hours, and in particular between about 2 and 15 hours and usually in the range of about 2 to 7 hours. The delivery of the agent formulation from the dispensing device, once begun, is continued until essentially all of the active agent formulation is dispensed. By "essentially all of the active agent formulation" is intended at least about 95% of the active agent formulation, preferably above about 97% and usually greater than 98% of the active agent is delivered to the fluid environment of use. The active agent formulation is preferably administered as a bolus, i.e., the dose of active agent in the device is released in a short period of time of one hour or less and usually within about 30 minutes and preferably within about 15 minutes of initiation of delivery of the active agent formulation.

By "semipermeable" is intended a material that is permeable to fluid but impermeable to other ingredients contained in the dispensing device and the environment of use. By "impermeable" is meant that the material is impermeable to fluids as well as to other ingredients contained in the dispensing device such that the migration of such materials into or out of the device is so low as to have substantially no adverse impact on the function of the device during the delivery period.

The term "active agent formulation" intends the drug or active agent optionally in combination with pharmaceutically acceptable carriers and additional inert ingredients. It is to be understood that more than one active agent may be incorporated into the active agent formulation in a device of this invention, and that the use of the term "agent" or "drug" in no way excludes the use of two or more such agents or drugs. The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The term "active agent" is used herein refers to an agent, drug, compound, composition of matter or mixture thereof which provides some biological, often beneficial, effect. This includes pesticides, herbicides, germicides, biocides, algaecides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active agent that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable active agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial active agents useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyidopa, dihydroxyphenylalanine, theophylline, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the terms "therapeutically effective" amount or rate refer to the amount or rate of the active agent needed to achieve the desired therapeutic result.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

FIG. 1 depicts, in side cross-sectional view, an embodiment of the delivery device according to the present invention. The device is shown in closed or prepared form prior to placement in the environment of use. Dispensing device 1 comprises a first housing 8 and a closure 10. Housing 8 and closure 10 in this particular embodiment are shown to be a first impermeable housing 12 and a second semipermeable housing 14 which are in slidably telescoping arrangement with each other. First housing 12 contains a first expansion agent 20 and an active agent formulation 22. The expansion agent 20 and the active agent formulation 22 do not completely fill the interior of housing 12, instead, housing 12 is dimensioned to provide a fluid flow path 24 between the inner wall of housing 12 and its contents to facilitate rapid fluid entry after separation of the housings and rapid expansion of expansion agent 20 and delivery of active agent formulation 22. FIG. 1 shows the flow path 24 between the inner wall of housing 12 and both the active agent formulation 22 and the first expansion agent 20, but the flow path may be limited to the area between the active agent formulation 22 and the housing 12.

Second housing 14 contains a second expansion agent 30 and an impermeable partition 32 that is positioned between the second expansion agent 30 and the open end 36 of first housing 12. First housing 12 and second housing 14 at their ends are close in size so that a friction fit is formed between the housings. The friction generated is sufficient to maintain the two housings together prior to activation of the second expansion agent 30 but not so great as to keep the two housings from sliding apart once an expanding driving force is exerted. The end of first housing 12 is adapted to fit within second housing 14. The edge 34 of the end of first housing 12 provides a platform or ridge against which partition 32 abuts to receive the driving force of second expansion agent 30 to separate the two housings.

Figure 2:
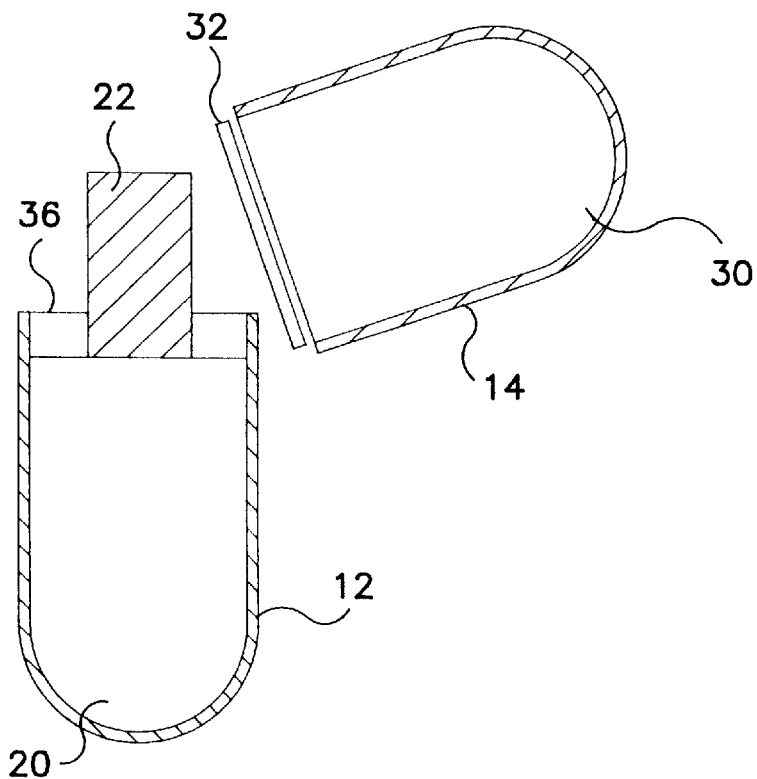
FIG. 2 shows the device of FIG. 1 in operation with the first expansion agent expanded and the active agent formulation being delivered to the environment.

In operation, dispensing device 1 is placed in the fluid environment of use and second expansion agent 30 begins to imbibe and absorb fluid from the environment through the semipermeable wall of the second housing 14. Second expansion agent 30 expands, exerting a driving force via partition 32 against edge 34 of first housing 12 and the end of formulation 22 to slidably separate first housing 12 from second housing 14. Following separation of the first housing 12 and second housing 14, fluid from the environment of use enters the open end 36 of first housing 12 and flow path 24, thus causing first expansion agent 20 to imbibe fluid. As first expansion agent 20 imbibes fluid, it expands and pushes against active agent formulation 22. As shown in FIG. 2, formulation 22 is expelled from housing 12 into the environment of use, within an hour, preferably within about 30 minutes and usually within about 15 minutes of the separation of the two housings.

Figure 3:
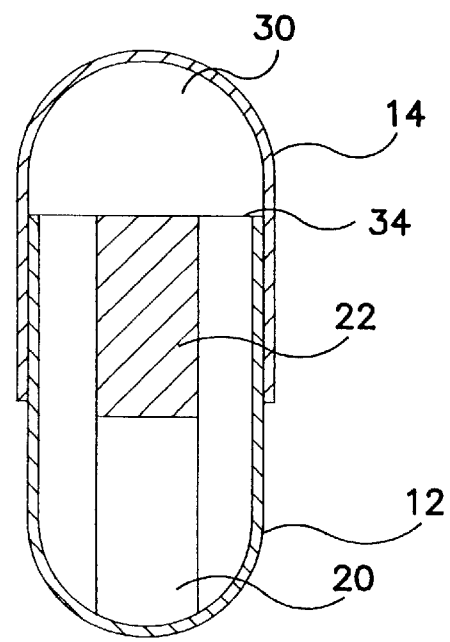
FIG. 3 is a side cross-sectional view of a second embodiment of the delivery device according to the present invention, the device being in closed or prepared form prior to placement in the environment of use.

FIG. 3 shows, in side cross-sectional view, a further embodiment of the delivery device according to the present invention. In this embodiment, the partition 32 shown in FIGS. 1–2 has been omitted and the expansion agent 30 pushes directly against edge 34 and active agent formulation 22 to accomplish separation of housings 12 and 14.

Figures 4, 5:
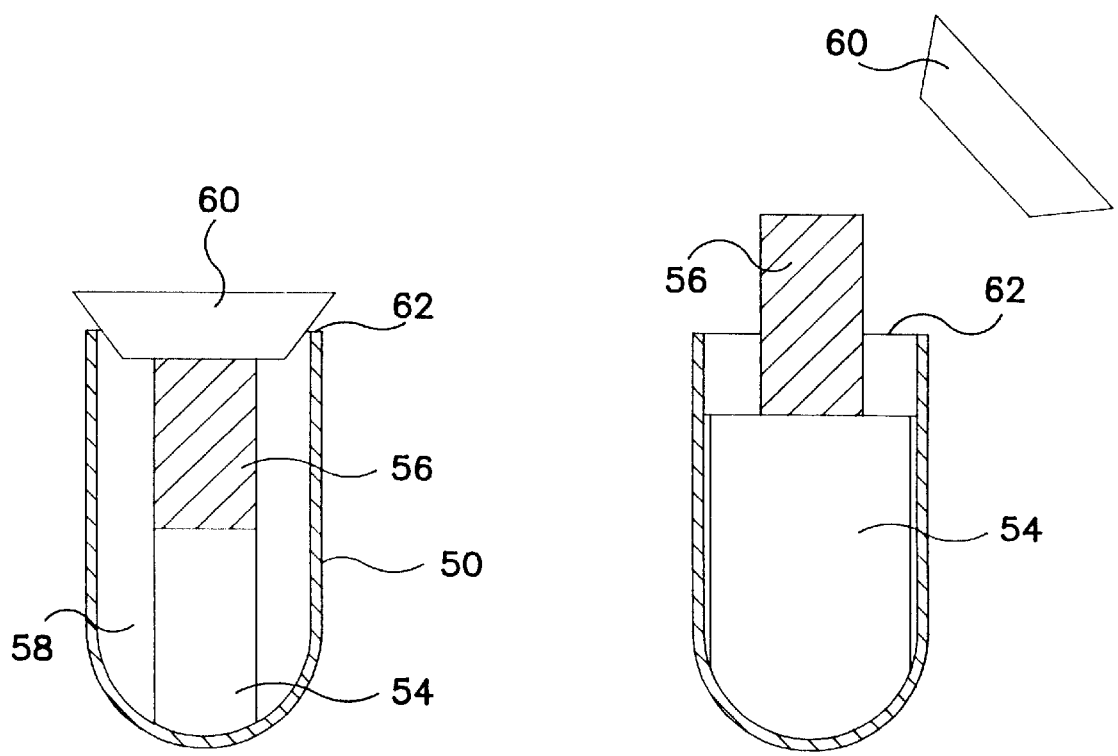
FIG. 4 is a side cross-sectional view of yet another embodiment of the delivery device of the present invention, the device being in closed or prepared form prior to placement in the environment of use.
FIG. 5 shows the device of FIG. 4 in operation with the expansion agent expanded and the active agent formulation being delivered to the environment.

FIG. 4 shows, in side cross-sectional view, yet another embodiment of the delivery device according to the present invention. In this embodiment, a housing 50 contains an expansion agent 54 and an active agent formulation 56. Similar to the devices shown in FIGS. 1–3 above, the expansion agent 54 and the active agent formulation 56 do not completely fill the interior of housing 50. Instead, a fluid flow path 58 that facilitates fluid entry into the housing 50 and delivery of the active agent formulation 56 is defined between the interior of the housing 50 and the active agent formulation 56 and the expansion agent 56. FIG. 4 shows the flow path 58 between the inner wall of housing 50 and both the active agent formulation 56 and the expansion agent 54, but the flow path may be limited to the area between the active agent formulation 56 and the housing 50. A second expansion agent in the form of a plug 60 is a closure that seals the open end 62 of housing 50. Upon insertion in the fluid environment of use, the plug 60 swells and separates from the housing 50 thereby permitting fluid entry into the chamber.

FIG. 5 shows delivery of the active agent formulation 56 and expansion of the expansion agent 54. Devices such as that described in FIGS. 4–5 are more fully detailed in EPA 384642 which is incorporated by reference herein.

Because first expansion agents 20 and 54 operate by imbibing fluid that enters the fluid flow paths 24 and 58 via open ends 36 and 62 of the housings 12 and 50, respectively, the wall of first housings 12 and 50 are preferably comprised of an impermeable material in at least the portion of the housing that is in contact with the first expansion agents 20 and 54. In this way, the first expansion agents 20 and 54 are not prematurely activated. When an active agent or an active agent dosage form is sensitive to fluid from an exterior fluid present in the environment of use, it is preferred that first housings 12 and 50 be substantially impermeable in their entirety to the ingress of the external fluid to serve as a means for substantially protecting the active agent formulations 22 and 56 as well as the first expansion agents 20 and 54.

Because second expansion agent 30 operates by imbibing external fluid while the housings 12 and 14 remain telescopically connected, the wall of second housing 14 in at least the portion that is adjacent to second expansion agent 30 must be semipermeable.

The walls of housings 12, 14 and 50 optionally comprise additional ingredients such as, for example, a plasticizer. Impermeable and semipermeable compositions suitable for use in housings 12, 14, and 50 as well as suitable additives, are known in the art, examples of which are disclosed in U.S. Pat. No. 4,874,388, which is incorporated herein by reference.

The delivery devices of the present invention are nontoxic, biologically inert, nonallergenic and nonirritating to body tissue, and maintain their physical and chemical integrity; that is, the devices do not erode or degrade in the environment of use during the dispensing period. It is within the scope of the invention that the devices be insoluble only during the period of intended use and can thereafter dissolve away in the environment of use. Thus, a dispenser is contemplated which is unaffected by its environment, solubility-wise, at the situs of use or which, alternatively, is only slightly soluble during the period of intended use, such that once its active agent content has been removed it will then dissolve or erode away.

The first and second expansion agents 20, 30, 56 and 60 are nontoxic, nonallergenic and biologically inert. The first and second expansion agents in each device may be the same or they may be different. In one embodiment, the expansion agents comprise an osmopolymer. Osmopolymers interact with water and aqueous biological fluids and swell or expand to an equilibrium state. Osmopolymers exhibit the ability to swell in fluid and to retain a significant portion of the imbibed and absorbed fluid within the polymer structure. The expansion agents in another embodiment comprise an osmagent. Osmagents are also known as osmotically effective solutes and compounds. Osmagents that can be used for the purpose of this invention include inorganic and organic compounds that exhibit an osmotic pressure gradient across a semipermeable, i.e., a fluid-permeable wall. The expansion agents in yet another embodiment comprise an osmagent dispersed within an osmopolymer. The expansion agents can be in tablet or layer form, or can be a plurality of tablets or layers. The osmagent or osmopolymer can be in any suitable form such as particles, crystals, pellets, granules, porous hydrogels, elastic polymeric sponges and the like. Osmagents and osmopolymers are known to the art and are described in, for example, U.S. Pat. Nos. 3,865,108, 4,002,173, 4,207,893, 4,327,725 and 4,612,008, which are incorporated by reference herein.

Partition 32 may comprise a composition that is substantially impermeable to the passage of fluid and that restricts passage of fluid present in the second expansion agent into the first housing. It operates to essentially maintain the integrity of the active agent formulation 22 and the first expansion agent 20. Additionally, partition 32 transmits the expanding driving force generated by the second expansion agent 30 directly against first housing 12 to separate the first and second housings. Thus, partition 32 must be of sufficient strength, thickness and rigidity to transfer the driving force onto first housing 12. Representative impermeable materials useful as partition 32 are known to the art and described in, for example, U.S. Pat. No. 4,874,388 which is incorporated herein by reference.

The active agent formulation comprises the active agent to be delivered, generally in a pharmaceutically acceptable carrier and with or without additional inert ingredients. The active agent formulation may additionally include dosage forms comprising the active agent that are capable of maintaining their physical configuration and chemical integrity while housed within the dispenser. These include, without limitation, tablets with or without a density element; matrix tablets; spheres; pellets and elongated tablets; capsules; elementary osmotic pumps, such as those described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which patents are incorporated herein by reference.

The pharmaceutically acceptable carrier may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874, which is incorporated by reference herein. In a further embodiment, the formulation may include an osmotic agent or solute, such as those described above with reference to the expansion agent, so that when the formulation comes into contact with the environmental fluid, it immediately dissolves. Suitable materials useful as active agent carriers and excipients are known in the art and are disclosed, for example, in U.S. Pat. Nos. 4,595,583 and 4,874,388, which are incorporated by reference herein.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect but will be between 0.01 ng and 500 mg.

For proper delivery of the active agent, it may be desirable in some instances for the dispensing device to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388, which is incorporated by reference herein. When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivacause nausea or bleeding by or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolve once they arrive at the small intestine, thereafter allowing fluid to be imbibed to activate the dispensing device. Enteric coatings are well known in the art and are discussed in, for example, "Remington's Pharmaceutical Sciences", Mack Publishing Co., Easton, Pa.

The total delay time prior to separation of the housing and closure of the dispensing device and the total delivery time of the active agent formulation can be controlled by a number of means to provide a sharp start-up of delivery at a particular time with high accuracy. For example, the rate of fluid inhibition into each of the expansion agent, and thus the rate of expansion of the expansion agent, can be controlled by the particular choice of semipermeable membrane or microporous screen. The rate of expansion of the expansion agent can also be controlled by the choice of composition of the expansion agent. The distance of overlap between the telescoping portions of the housing and closure can determine the period of time required for the housing and closure to separate. Combinations of such control means may be used. Such control means are known in the art and can be determined without undue experimentation.

The fluid flow paths 24 and 58 are formed between the active agent formulation 22 and the interior of housings 12 and 50 and may extend to the area between the first expansion agents 20 and 54 and the housings 12 and 50. The space occupied by the fluid flow path is at least 5% of the interior cross-sectional area of the housing, usually between about 5 and 75% of the cross-sectional area and often between 20 and 60% of the cross-sectional area.

The delivery device of the present invention can be manufactured by standard manufacturing techniques. For example, in the preparation of devices of the present invention, first housing 12 and second housing 14 may be separately molded or extruded to the desired shape. Possible semipermeable materials from which the second housing 14 may be prepared include, for example, Hytrel® polyester elastomers (Du Pont), cellulose esters, water flux enhanced ethylene-vinyl acetate copolymers, semipermeable membranes made by blending a rigid polymer with water-soluble low molecular weight compounds, and other semipermeable materials known to the art. Impermeable materials from which the first housing 12 may be prepared include, for example, polyethylene, polystyrene, ethylene-vinyl acetate copolymers, Hytrel polyester elastomers (Du Pont) and other impermeable materials known to the art. Alternatively, the two portions of a hard gelatin capsule may be coated, one with an impermeable material and the other with a semipermeable material such as cellulose ester-based polymer mixtures. In a presently preferred embodiment, the assembled device in closed configuration is about the size and dimensions of a size "3" to size "OO" hard gelatin capsule.

Expansion agent 20 is prepared from an osmotic material and formed into a shape that will fit within housing 12 with clearance between the expansion agent and the vessel wall. The layer is compressed into a tablet on a rotary bilayer tablet press. Expansion agent 30 is prepared from an osmotic material and partition 32 is prepared from an impermeable material. Both are formed into a shape that will fit within housing 14, and compressed on a bilayer rotary tablet press.

With reference to FIG. 1, the device is assembled as follows. Expansion agent 20 is inserted into the vessel 12 at its end opposite its open end 36. Active agent formulation 22 is then placed on top of expansion agent 20. The expansion agent 30 and partition 32 are placed within the cap 14 and the cap assembly is placed over the end of the filled vessel 12 so that partition 32 is adjacent to the open end of the filled vessel 12.

The following examples are illustrative of the present invention. They are not to be construed as a limitation of the scope of the invention. Variations and equivalents of these examples will be apparent to one skilled in the art in light of the present disclosure, the drawings and the claims herein.

EXAMPLE 1

Delivery devices for delivering 125 mg of a progesterone formulation into the colon for hormone replacement therapy according to the present invention were prepared as follows.

The first housing, with one closed end and one open end was prepared by placing pelletized ethylene vinyl acetate copolymer (EVA, 9 wt. % vinyl acetate) in an extruder with a barrel temperature of 130° C. to form a vessel having a 0.762 cm ID and a 0.876 cm OD. An expansion agent tablet was then placed in the first housing. The tablet was prepared from 125 mg of Crospovidone XL-10 (International Specialty Products, Wayne N.J.) powder which had been compressed in a rotary press to have a diameter of 0.556 cm and a length of 0.556 cm. A fluid flow path between the tablet and the inner wall of the housing measured 0.206 cm. An active agent formulation tablet was placed on top of the expansion agent tablet. The 125 mg active agent formulation tablet contained 80 wt. % progesterone, 10 wt. % Crospovidone XL-10 (International Specialty Products, Wayne N.J.) and 10 wt. % polyoxyethylene 40 stearate (ICI America International, Wilmington, Del.). The formulation was prepared by screening the components through a 40 mesh screen, mixing with ethanol to form a wet mass, screening through a 20 mesh screen, and oven-drying at 40° C. for 24 hours. Magnesium stearate (0.5 wt. %) was added. The resultant active agent formulation was compressed in a rotary press into cylindrical tablets having a diameter of 0.556 cm and a length of 0.556 cm. The tablet was placed into the first housing leaving a fluid flow path between the active agent formulation tablet and the inner wall of the first housing of 0.206 cm. The flow path occupied 46% of the interior cross-sectional area of the housing.

The second housing was formed from a clear, size O gelatin capsule. A second expanding layer of the device was formed from the following dry components: 58.75 wt. % sodium carboxymethyl cellulose (NaCMC), 30 wt. % NaCl, 5.0 wt. % hydroxypropylmethyl cellulose E-5 (Aqualon, Wilmington, Del.), and 1.0 wt. % red ferric oxide. After mixing for 10 minutes, 5.0 wt. % HPC-EF (Aqualon, Wilmington, Del.), dissolved in purified water was sprayed onto the dry components to prepare granules. Magnesium stearate (0.25 wt. %) was added and the second expanding layer granules were thoroughly mixed for 5 min. An impermeable partition was formed by screening 95 wt. % hydroxypropylmethyl cellulose E-5 (Aqualon) and 5.0 wt. % stearic acid using a 40 mesh screen. The screened materials were added to a Hobart mixer and blended for 10 minutes. Ethanol was added until a wet mass was formed. The wet mass was screened through a 20 mesh screen and allowed to air dry for 12 hours. The granules were then passed through a 20 mesh screen. 200 mg of the expanding layer granules and 50 mg of the partition layer granules were compressed together into a bilayer tablet in a rotary press. The tablet was placed into the gelatin capsule, expanding layer side down. Polyvinylpyrrolidone (PVP k29-32, International Specialty Products) was dissolved in methanol and sprayed onto the capsule as a 2 mg subcoating. 75 wt. % cellulose acetate 398-10 (Eastman Chemical, Kingsport, N.J.) and 25 wt. % polyethylene glycol 3350 (Union Carbide, Danbury, Conn.) was dissolved in an acetone/methanol (80/20 wt/wt) solution. This 4 wt. % solid solution was sprayed onto the subcoating to form a 70 mg semipermeable membrane. The second housing was dried at 50° C. and 50% RH for 72 hours and then at 50° C. and ambient RH for 24 hours. The open end of the second housing was fitted over the open end of the first housing and the two housings were compressed together.

EXAMPLE 2

Eight devices were prepared as described in Example 1. The systems were orally administered to fasted dogs by placing the systems deeply into the oral pharynx of the dogs so that they were swallowed intact. Water was administered immediately following dosing to ensure passage of the system into the stomach.

The dogs were monitored at regular intervals during the normal work day. At each observation, any fecal material that was found in the cages was carefully examined for the presence of the system. The time of recovery of the system was used to estimate the transit time of the device.

Table 1 shows the transit times and amount recovered from these 8 devices.

TABLE I

| System # | Transit time (hr.) | Progesterone Residual % |
|---|---|---|
| 1 | 24.5–24.7 | 0.9 |
| 2 | 24.5–24.7 | 0.3 |
| 3 | 24.5–24.7 | 3.9 |
| 4 | 48.8–50.5 | 0.0 |
| 5 | not recovered | N/A |
| 6 | 26.7–28.2 | 0.0 |
| 7 | 26.7–28.2 | 0.7 |
| 8 | 26.7–28.2 | 0.1 |

TABLE I-continued

As can be seen from Table 1, although transit times vary with the individual dogs, the devices delivered greater than 95% of the active agent formulation in a predictable manner. When similar devices were made with no fluid flow path between the housing and the active agent formulation, the delivery was not as predictable since the amount of active agent formulation remaining in the device varied from 0–82%.

The above description has been given for ease of understanding only. No unnecessary limitations should be understood therefrom, as modifications will be obvious to those skilled in the art.

What is claimed is:

1. A fluid-imbibing delivery device for dispensing an active agent formulation to a fluid environment of use after an initial, preset delay of startup of delivery, the device comprising a housing and a closure for the housing, the housing containing an active agent formulation comprising at least one active agent and a first expansion agent, the housing and the active agent formulation being configured to provide a fluid flow path between the interior of the housing and the active agent formulation, and the closure comprising a second expansion agent.

2. The device of claim 1 wherein the housing is an impermeable housing and the closure comprises a semipermeable housing in reversibly sliding telescoping relation with the impermeable housing.

3. The device of claim 1 wherein the first and second expansion agents are selected from the group consisting of osmagents, osmopolymers and mixtures thereof.

4. The device of claim 1 comprising a partition disposed between said second expansion agent and said active agent formulation.

5. The device of claim 1 wherein the active agent formulation comprises progesterone.

6. The device of claim 1 wherein the active agent formulation comprises human growth hormone.

7. The device of claim 1 wherein the closure comprises a plug in said housing.

8. The device of claim 1 wherein said housing contains a second active agent formulation.

9. The device of claim 1 that further comprises an enteric coating.

10. The device of claim 1, wherein the first housing has an interior cross-sectional area and the fluid flow path occupies 5–75% of the interior cross-sectional area of the first housing.

11. In a fluid-imbibing delivery device for dispensing an active agent formulation to a fluid environment of use after an initial, preset delay of startup of delivery, the device comprising a housing having a closed end and an open end, the housing containing an active agent formulation comprising at least one active agent and an expansion agent, and a plug sealing the open end of the housing;

the improvement comprising a fluid flow path between the active agent formulation and the interior of the housing.

12. The device of claim 11 that further comprises an enteric coating.

13. The device of claim 11, wherein the housing has an interior cross-sectional area and the fluid flow path occupies 5–75% of the interior cross-sectional area of the housing.

14. The device of claim 11, wherein the plug comprises a second expansion agent.

15. In a fluid-imbibing delivery device for dispensing an active agent formulation to a fluid environment of use after an initial, preset delay of startup of delivery, the device comprising a first impermeable housing and a second semi-permeable housing, the first and second housings being in reversibly sliding telescoping arrangement with each other, the first housing containing an active agent formulation comprising at least one active agent and a first expansion agent, and the second housing containing a second expansion agent;

the improvement comprising a fluid flow path between the active agent formulation and the interior of the first housing.

16. The device of claim 15 that further comprises an enteric coating.

17. The device of claim 15, wherein the first housing has an interior cross-sectional area and the fluid flow path occupies 5–75% of the interior cross-sectional area of the first housing.

* * * * *